United States Patent [19]

Zeitels

[11] Patent Number: 5,092,314
[45] Date of Patent: Mar. 3, 1992

[54] ADJUSTABLE SUPRAGLOTTISCOPE AND METHODS THEREFOR

[76] Inventor: Steven M. Zeitels, 20 Burroughs St., Jamaica Plain, Mass. 02130

[21] Appl. No.: 520,647

[22] Filed: May 8, 1990

[51] Int. Cl.5 .............................................. A61B 1/26
[52] U.S. Cl. ...................................................... 128/10
[58] Field of Search ........................ 128/10, 11, 15-18

[56] References Cited

U.S. PATENT DOCUMENTS

| | | | |
|---|---|---|---|
| 4,086,919 | 5/1978 | Bullard | 128/11 |
| 4,384,570 | 5/1983 | Roberts | 128/4 |
| 4,611,579 | 9/1986 | Bellhouse | 128/11 |
| 4,681,094 | 7/1987 | Rolnick | 128/10 |
| 4,832,020 | 5/1989 | Augustine | 128/10 |
| 4,947,896 | 8/1990 | Bartlett | 128/11 |
| 4,982,729 | 1/1991 | Wu | 128/11 |

FOREIGN PATENT DOCUMENTS

| | | | |
|---|---|---|---|
| 0339541 | 11/1989 | European Pat. Off. | 128/11 |
| 3217476 | 12/1982 | Fed. Rep. of Germany | 128/17 |

OTHER PUBLICATIONS

Catalog, V. Mueller & Co., Chicago, Ill., pp. 654–655, 1963.

Karl Storz catalog; Lindholm Laryngoscope; Model No. 8587, p. A15 (1987).

Karl Storz catalog; WEERDA Distending Operating Laryngoscope, Model No. 8588 (1987).

Richard Wolf catalog; Steiner Adjustable Laryngo--Pharyngoscope, Model 8456, pp. G33-G34 (1984).

Weerda, H. et al., "A New Distending Larynogoscope for Diagnosis and Microsurgery of the Larynx", *Laryngoscope*, 93: 639–641 (1983).

Primary Examiner—Stephen C. Pellegrino
Assistant Examiner—Ralph A. Lewis
Attorney, Agent, or Firm—Cohen, Pontani & Lieberman

[57] ABSTRACT

An adjustable supraglottiscope designed to be used in the supraglottic larynx is disclosed, in particular, an improved apparatus for endoscopic surgery in the supraglottis and the lower pharynx is disclosed by having at least one blade that is at least as wide as the normal, human epiglottis in its natural position within the body. The blades of the supraglottiscope have a length to width ratio that is about one-half of that found in conventional instruments. This unique ratio enables a wider exposure of the supraglottic larynx and lower pharynx. Methods of performing surgery on the supraglottic larynx of a patient are also described.

11 Claims, 3 Drawing Sheets

ADJUSTABLE SUPRAGLOTTISCOPE AND METHODS THEREFOR

BACKGROUND

Laryngoscopes are routinely used to facilitate endotracheal intubation of patients, to provide an air passage for administration of anesthesia and/or to establish an airway that is obstructed. In addition, laryngoscopes are commonly used in surgery to displace pharyngeal tissues to permit direct inspection of the larynx (i.e. direct laryngoscopy).

Anesthesiologists use laryngoscopes that are L-shaped having a handle connected to single curved or straight blade. Otolaryngologists typically use a tubed laryngoscope to view the larynx and operate endoscopically on the true vocal cords (i.e. glottis).

Modern adjustable laryngoscopes, the forerunners of which first appeared in the early decades of the twentieth century, are all bivalved glottiscopes designed for use on the true vocal cords. They characteristically possess long and narrow blades. Adjustable glottiscopes are designed to be inserted into the mouth and down the throat. The superior blade engages the tongue and supraglottis while the inferior blade engages the roof of the mouth and the posterior pharyngeal wall. The length of the blades allows for exposure of the true vocal cords. Examples of such laryngoscopes include the Weerda Laryngoscope (Karl Storz Co., Culver City, Calif.) and the Steiner Laryngoscope (Richard Wolf Co., Rosemont, Ill.). They are conveniently used for surgery in the lower larynx (true vocal cords/glottis).

Nevertheless use of these instruments may be ineffective for surgery in the supraglottis (epiglottis and false vocal cords) and lower pharynx (base of tongue, pharyngoepiglottic folds, and posterior pharyngeal wall). This is due primarily to the length and the narrowness of the adjustable blades of conventional adjustable glottiscopes. In addition, when exposing the larynx, these conventional instruments are designed to extend both the head and neck by tilting the head backwards and distending the lower jaw. Adequate exposure of the supraglottis for endoscopic surgery, especially with the carbon dioxide laser, requires true suspension which involves flexion of the neck, while extending the head (the "sniffing" position).

Most significantly, the distal lumen of conventional adjustable glottiscopes, formed by the ends of the long and narrow blades, has a surface area that is small in relationship to the surface area of the supraglottis. Endoscopic laser surgery of the supraglottis is precluded by conventional adjustable glottiscopes because there is insufficient exposure of the supraglottic surgical field.

SUMMARY OF THE INVENTION

This invention pertains to an improved apparatus specifically designed for endoscopic surgery in the supraglottis and lower pharynx and methods of using this apparatus. This improved apparatus, called an adjustable supraglottiscope, enables effective endoscopic surgery of the supraglottic larynx and lower pharynx. The adjustable supraglottiscope allows for wider visualization of the surgical field. This enables the surgeon to manipulate the tissue within the endoscopic surgical field to alter the particular operative site. This saves time because the laryngoscope can be left in place rather than repeatedly reinserting and repositioning the instrumentation.

The improvement comprises a modification of the blades of conventional laryngoscopes to enable a wider exposure of the supraglottic larynx and lower pharynx. The superior blade is designed to be at least as wide as the normal, human epiglottis in its natural position within the body. Both blades of the adjustable supraglottiscope have a length to width ratio sufficient to expos the supraglottic larynx when the blades are engaged in the laryngopharynx and urged apart. The length to width ratio of the blades is about one half of that found in conventional instruments. The unique length to width ratio of the blades of the adjustable supraglottiscope enables a variety of surgical procedures to be performed that were not heretofore practical or possible. The adjustable supraglottiscope also comprises a handle specifically designed to be used with laryngoscope suspension systems, such as the Boston University suspension system.

Methods of surgical operation using the adjustable supraglottiscope of this invention comprise, inserting the supraglottiscope, engaging the blades with at least part of the roof of the mouth and at least part of the base of the tongue, separating and distending the blades sufficiently to expose the supraglottis, and engaging the laryngoscope with a suspension system. In practice, the superior blade of the adjustable supraglottiscope can be placed in a variety of positions: in the vallecula (for supraglottic or aryepiglottic fold exposure); under the epiglottis (for false vocal cord exposure); just before the vallecula to expose the base of the tongue; with the superior blade behind the larynx to expose the posterior pharyngeal wall; or with each blade above and below the pharyngoepiglottic fold.

The above and other features of the invention will now be more particularly described with reference to the accompanying drawings as pointed out in the claims. It will be understood that the particular supraglottiscope embodying the invention is shown by way of illustration only and not as a limitation of the invention. The principles and features of this invention may be employed in various and numerous embodiments without departing from the scope of the invention.

DETAILED DESCRIPTION OF THE INVENTION

This invention pertains to an improved laryngoscope, called an adjustable supraglottiscope, designed to facilitate surgery of the supraglottic larynx and lower pharynx and the methods for its use. In particular, this invention pertains to an adjustable laryngoscope which provides a much larger endoscopic surgical field. The configuration of the upper blade is such that a surgeon can choose to place it in the vallecula, under the epiglottis, or behind the larynx. The other blade of the supraglottiscope maintains the endotracheal tube out of the operative field. This invention also pertains to an adjustable supraglottiscope in which the lumen defined by the blades in their fully opened position is such that the proximal and distal working areas of the supraglottiscope are significantly greater than the respective working areas of conventional laryngoscopes. Further, the supraglottiscope has a handle designed to be used with suspension systems.

The adjustable supraglottiscope and methods of the invention are designed to facilitate surgery in particular regions of the body, defined collectively and interchangeably as the "supraglottic larynx", "lower oropharynx" or "upper hypopharynx." Briefly, the supraglottiscope is designed to facilitate, surgery of the lower pharynx, which is that part of the alimentary canal which is placed behind the mouth and larynx. Surgery is faciliated in the oral part of the pharynx, as the oropharynx (the base of the tongue and posterior pharyngeal wall). The supraglottiscope can also be used for surgery in the hypopharynx (the pharyngo epiglottic larynx, medial wall(s) of the pyriform sinus, and posterior pharyngeal wall), which is that part of pharynx that extends below the level o the epiglottis, where it is continuous with the esophagus. Further, the supraglottiscope is designed for use in the supraglottic larynx (lingual and laryngeal surfaces of the epiglottis, false vocal cords, aryepiglottic folds, and arytenoid cartilages). See also *Gray's Anatomy*, Commemorative Edition, pages 869–870, Bounty Books, New York (1977) incorporated herein by reference.

Figure 1:
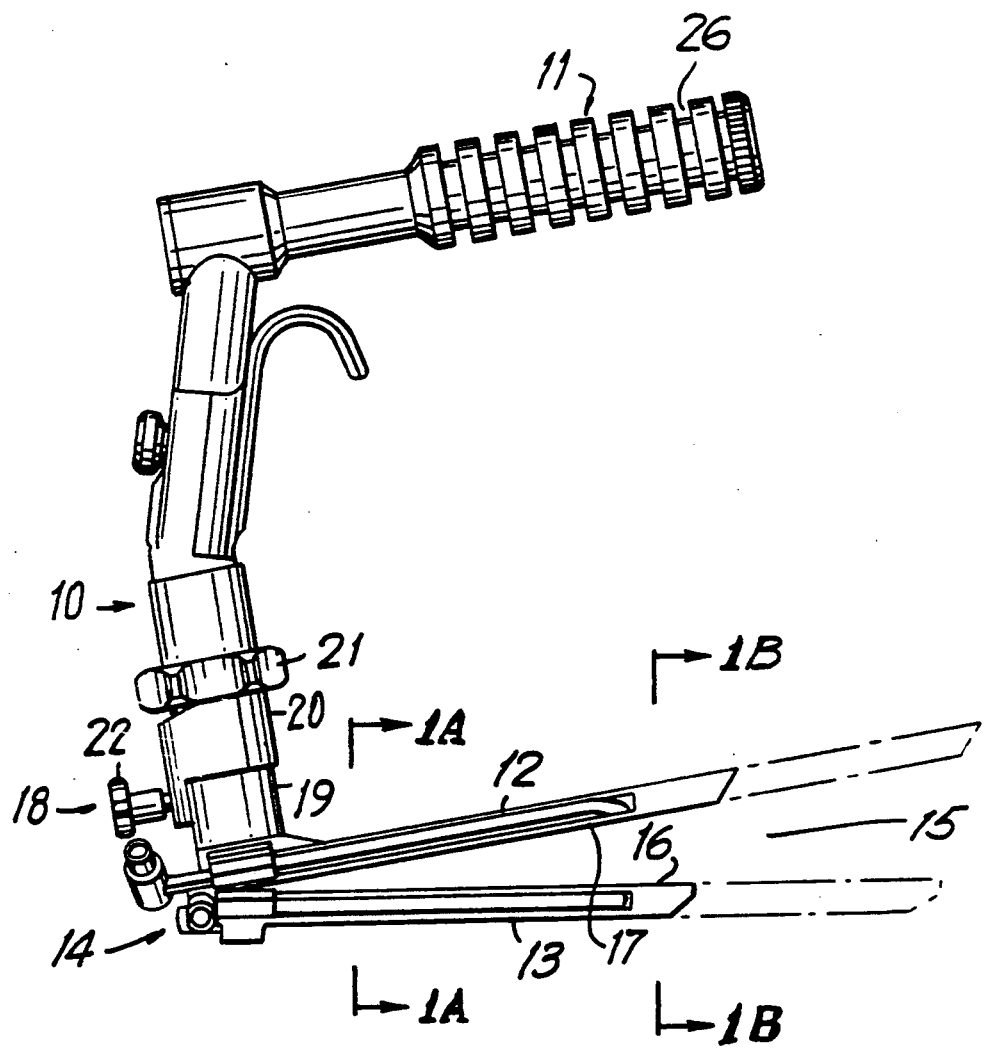
FIG. 1 is a side view of the supraglottiscope of this invention.

FIG. 1 illustrates the laryngoscope of this invention with the conventional blade means of the prior art (exemplified by the Steiner Laryngoscope Model No. 8456.01) drawn to scale and superimposed in phantom lines. The adjustable supraglottiscope 10 comprises a handle 11 connected to a pair of opposed, substantially parallel blades, 12 and 13. The blades have a proximal end 14 and a distal end 15. Each blade has a shaped interior surface 16 (FIG. 2) that runs the full length of the blade. The interior surface of the blades may define a rectangular shape, although the shape of the interior surface configuration may be other than rectangular. Preferably, each blade has a transversely arcuate configuration designed to follow the transverse contours of the normal, human epiglottis in its natural, curved position. Each blade can also be used with adjustable self-contained suction and light carriers that clip onto the blades.

Figure 2A:
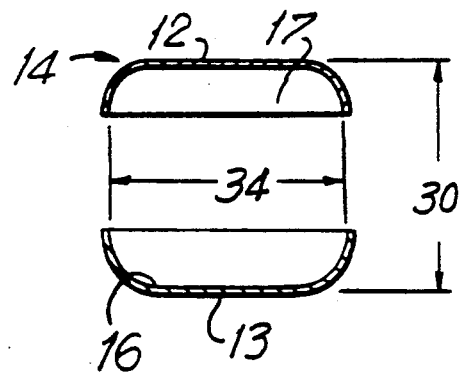
FIGS. 2A and 2B are cross-sectional views along the lines 1A and 1B, respectively in FIG. 1 illustrating the dimensions (in millimeters) of the proximal and distal lumenal openings of the supraglottiscope respectively.
Figure 2B:
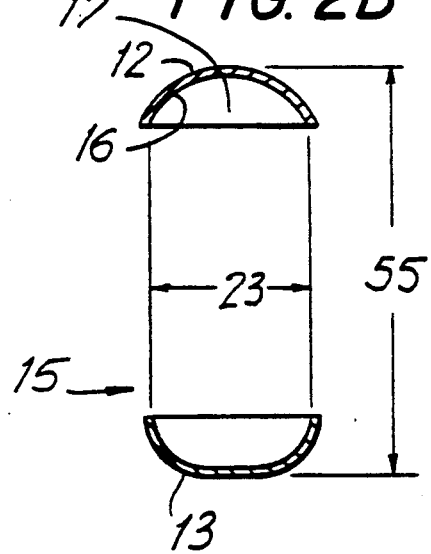

The parallel walls of blades 12 and 13 have arcuate edges which, on separation, define a substantially rectangular lumen 17, as illustrated in FIGS. 2A and 2B. This lumen 17 is designed to receive various instruments during surgery, such as endotracheal tubes, retractors, forceps, probes, suction devices and the like. The sides of the lumenal openings in FIGS. 2A and 2B shown by the dashed lines, represent the surfaces of rectangular, malleable retractors. In use, the retractors can be optionally inserted on the sides of distended blades, in a position substantially perpendicular to the superior 12 and inferior 13 blades. This configuration thus defines a substantially rectangular shape, wherein the blades define the top and bottom sections of the rectangle and the retractors define the remaining sides. The retractors are used to keep pharyngeal tissues out of the operative field.

The blades are moved by any adjustable means 18 for urging the blades apart. The means may be of the type used in the Steiner laryngoscope (Richard Wolf Co., Rosemont, Ill.). Typically, adjustable means capable of being used with the invention comprise a rod or projection 19 attached to the blades near the proximal ends 14 thereof. This rod 19 is affixed to, and is substantially perpendicular to, the superior blade 12. The rod 19 is moveably engaged with a tubular sleeve 20 formed as an extension of the handle 11. A threaded nut 21 is positioned adjacent to the lower end of the sleeve 20 and is designed to receive the rod 19. The nut 21 cooperates with a threaded section of the rod. Rotating the nut serves to move the rod 19 axially within the sleeve 20. The adjustable means also comprises a screw 22 that cooperates with a means for urging the inferior blade 13 in an inferior direction once the blades have been initially distended. Preferably, in such arrangements the means for adjusting the blades is interposed between the handle 11 and the blades 12, 13 near the proximal end 14.

The blades of the supraglottiscope comprise a superior blade 12, designed to be engaged with at least part of the base of the tongue, and an inferior blade 13, designed to engage with at least part of the roof of the mouth. The blades can be urged apart using an adjustable means as described above.

Referring again to FIG. 1, the improved blade means are shorter and wider than all conventional laryngoscopes known in the art. The width of both blades, in particular the superior blade, is designed to be at least equal to, or wider than, the normal adult epiglottis. In its natural position within the body, the epiglottis is curved. The width of the supraglottiscope is designed to be consistent with the curved contours of the elastic cartilage that comprises the epiglottis. Thus, the superior blade of the supraglottiscope can be placed either above or below the epiglottis.

In a particularly preferred embodiment of this invention, the width of at least the superior blade 12 is from about 22 to about 28 millimeters. This width is specifically designed to accommodate the normal adult epiglottis in its arched position within the body (22±3 mm), or in a flattened position (25±3 mm). Blades narrower than about 22 to about 28 mm will be unable to expose the supraglottis for effective endoscopic surgery.

Surgery in the supraglottic larynx is therefore facilitated by modification of the length to width ratio of the blades sufficient to expose the supraglottic larynx, and lower pharynx. The length to width ratio of the blades of the supraglottiscope in the present invention is about 4.1 to about 4.7. Table 1 summarizes the preferred dimensions of the adjustable supraglottiscope and compares them with dimensions of conventional laryngoscopes already used for surgery. The length to width ratio of the blades of the supraglottiscope of the invention is about one half that of conventional laryngoscopes.

TABLE 1

Comparison of Preferred Dimensions of Supraglottiscope and Known Prior Art Laryngoscopes

| Dimension | Present Invention | Steiner[b] | Lindholm[c] | Storz[d] |
|---|---|---|---|---|
| Lumenal Area | | | | |

TABLE 1-continued

Comparison of Preferred Dimensions of Supraglottiscope and Known Prior Art Laryngoscopes

| Dimension | Present Invention | Steiner[b] | Lindholm[c] | Storz[d] |
|---|---|---|---|---|
| (mm²) | | | | |
| Proximal | | | | |
| Closed | 510 | 288 | 254 | 270 |
| Distended | 1,020 | 558 | 254 | 484 |
| Distal | | | | |
| Closed | 415 | 288 | 227 | 240 |
| Distended | 1,380 | 846 | 227 | 765 |
| Blade Working Length (mm) | | | | |
| Superior | 110 | 159 | | 100 |
| Inferior | 95 | 140 | | 70 |
| Blade Width (mm) | | | | |
| Superior | 34–23 | 18 | | 17 |
| Inferior | 34–23 | 18 | | 10 |
| Length/Width | | | | |
| Superior | 4.7 | 8.8 | | 5.8 |
| Inferior | 4.1 | 7.7 | | 7.0 |

[a]Length/width ratio calculated using interpolated width at half length; proximal width (34 m); distal width (23 mm).
[b]Measurements taken on Steiner Adjustable Laryngo-Pharyngoscope, Model No. 8456.01.
[c]Lindholm Operating Laryngoscope, Model No. 8587, Large size, 18 mm. This is a one piece, tubed laryngoscope designed to be used in the supraglottal larynx.
[d]Weerda Distending Operating Laryngoscope, Karl Storz Co., Model No. 8588 B - Small adult size.

Merely scaling down conventional prior art laryngoscopes for use in the supraglottic larynx is inadequate because the blades will still be too narrow to maintain supraglottic tissue such as the epiglottis out of the visual field. This is illustrated in Table 1 with the Storz Small Adult laryngoscope (Model 8588B) designed for use in the vocal cords and glottis. Although the blade lengths are less than those of the supraglottiscope, the blade width is not broadened commensurate with its shorter length. The length to width ratio is therefore still greater than the supraglottiscope. The blade width of the Storz instrument provides inadequate exposure of the supraglottic larynx. The width of the superior blade is less than that of the normal, human epiglottis and the blade will be unable to fit into the arched contour of the normal epiglottis, thus allowing pharyngeal tissue to obscure the operative field.

It will be readily appreciated that blade dimensions for a pediatric supraglottiscope according to this invention can easily be determined based on routinely-obtained measurements of the epiglottic width of children.

The width of the superior 12 and inferior 13 blades will also vary as a function of the length to width ratio. The preferred width of the superior blade is about 22 to about 28 mm, enough to accommodate the width of the normal, human epiglottis.

The length of the superior 12 and inferior 13 blades may therefore vary, depending upon the patient. Nevertheless, the length to width ratio will remain between the preferred range of about 4.1 to about 4.7, regardless of the blade length. A preferred blade length for the normal adult is about 110 mm for the superior blade 12 and about 95 mm for the inferior blade 13.

The supraglottiscope has a lumen 17 defined by the superior 12 and inferior blades 13. The opening of the lumen will have a variable cross section. This is due to the width of the superior 12 and inferior 13 blades and the size of the opening when the blades are fully distended by the adjustable means 18. Table 1 also compares the proximal and distal cross-sectional areas of the supraglottiscope with the same dimensions for conventional laryngoscopes. The cross-sectional area of the lumen at the fully distended proximal end of the supraglottiscope is nearly twice that of conventional instruments. Preferably, the cross-sectional area of both the distal and proximal ends in the fully distended position is at least 1,000 square millimeters.

Because the adjustable means 18 of conventional laryngoscopes can introduce a bias into the distention of the blades so that the blades expand in an angular configuration with respect to each other, the distal end 15 can be wider than the proximal end 14 when fully expanded. Under these circumstances, the area dimensions of the distended proximal end of the supraglottiscope substantially define a rectangle. This is shown in FIGS. 2A and 2B with a preferred width of about 34 mm and a preferred height of about 30 mm. The fully opened distal end 15 is defined by an elongated oval whose preferred height is about 55 mm and whose preferred width is about 23 mm. As described previously, the dashed lines in FIG. 1 can represent the edges of malleable retractors.

Figure 2C:
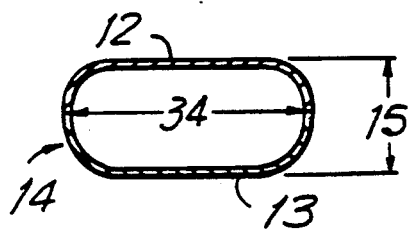
FIGS. 2C and 2D are cross-sectional views taken respectively along the lines 1A and 1B but illustrating the blades in a closed position.
Figure 2D:
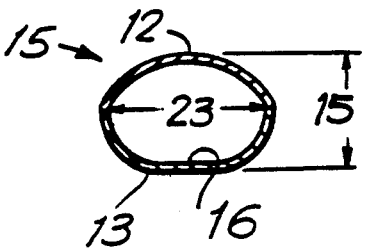

In a preferred embodiment, the proximal end 14 of both superior 12 and inferior 13 blades can also be wider than the corresponding distal end 15, thus providing the blades with a slight taper towards the distal end. In this embodiment, the blade width at the proximal end is at least 30 percent wider than the distal blade end width so that the cross-sectional opening of the proximal end in its closed position is necessarily greater than the corresponding cross sectional opening area of the distal end (see Table 1). Referring to FIG. 2C, the dimension of the closed proximal end 14 defines a rectangle with the shorter ends outwardly curved, about 34 mm in its longest side and about 15 mm in its shorter side. The closed distal end defines an oblate spheroid whose longer side is about 23 and whose shorter side is about 15 mm (FIG. 2D)

Figure 3:
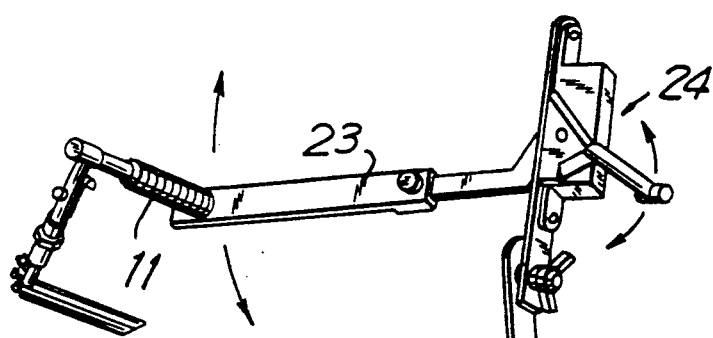
FIG. 3 shows the suspension system for use with the supraglottiscope.

As shown in FIG. 3, the handle 11 of the supraglottiscope is fashioned for use with suspension systems, such as the Boston University system. In such suspension systems, the patient's head and neck are lifted off the surface of the operating table by application of a lifting force substantially normal to the operating table. The force is transmitted to the patient by linking the handle 11 of the inserted supraglottiscope to an external frame 23. The external frame is connected to a lifting means 24 which is attached to the operating table 25, thus lifting the head, neck and shoulders of a patient off the table.

This system is particularly effective for laser microsurgery of the supraglottis. Using the adjustable supraglottiscope of this invention, the patient's neck is not hyperextended, as it is in most conventional laryngoscopy. Use of suspension facilitates exposure of the entire supraglottis. The handle 11 is substantially tubular. In a preferred embodiment, the handle has cut or incised therein a plurality of annular grooves 26 (FIG. 1) commencing at its free end and extending inwardly. These grooves are designed to detachably engage with corresponding projections on the suspension frame.

This invention also pertains to a method of performing surgery on a patient using the adjustable supraglottiscope. The supraglottiscope described herein can be utilized for a wide variety of surgical and other inspection techniques using a suspension-type system in conjunction with microscopic instrumentation including:

incisional and excisional biopsies; endoscopic airway palliation; staging of early supraglottic cancers and treatment with en bloc resection; excisions of laryngeal cysts; lingual tonsillectomy; laser arytenoidectomy; and management of supraglottic papillomatosis.

Figure 4:
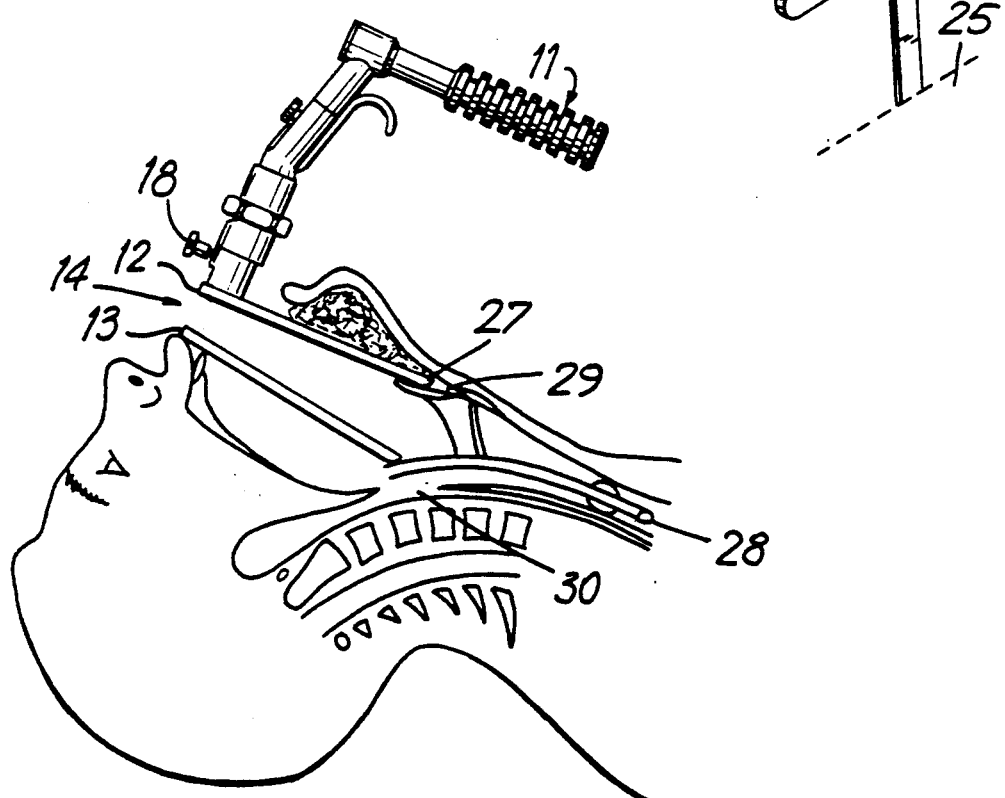
FIG. 4 shows a side view of the supraglottiscope of this invention in position for use.

The adjustable supraglottiscope is especially preferred for laser surgery using the Boston University suspension system. The wide exposure of the supraglottis and lower pharynx made available by the use of suspension is essential for effective laser surgery. Referring to FIG. 4, the preferred method of the invention involves inserting the supraglottiscope so that the superior blade is engaged with at least part of the tongue, for example the epiglottis 27 (either anterior or posterior to it), and the inferior blade 13 is engaged with at least part of the roof of the mouth. The proximal end 14 of the blades can protrude from the patient's mouth. The blades are then urged apart using the adjustable means 18 in order to distend the lumen defined by the superior 12 and inferior 13 blades. The head, shoulders, and neck of the patient is are then lifted off the operating table by the lifting means of the suspension system. Any endotracheal tube 28 can be kept out of the operative field by the inferior blade 13.

The unique shorter and wider blades of the supraglottiscope allow a surgeon some novel choices as to where to engage the distal end of the superior blade, choices that were not possible using conventional laryngoscopes. For example, exposure of the base of the tongue for laser lingual tonsillectomy can preferably be achieved by not inserting the superior blade 12 completely to the vallecula 29. Alternatively, the preferred method of performing laser surgery on the epiglottis 27 itself requires insertion of the superior blade 12 to the vallecular space 29 as embodied in FIG. 4. In practice, the superior blade 12 of the adjustable supraglottiscope can be placed in the vallecula 29 for exposure of the epiglottic and aryepiglottic folds, and/or the medial wall(s) of the pyriform sinus, under the epiglottis 27 for exposure of the false vocal cords and arytenoids, just proximal to the vallecula to expose the base of the tongue, behind the larynx to expose the posterior wall of the pharynx 30, or with one blade above and one blade below the pharyngoepiglottic fold.

After exposing the supraglottis with the adjustable supraglottiscope, an operating microscope fitted with a 400× lens can be used for improved visualization. For laser surgery, a carbon dioxide laser coupled to an operating microscope can be positioned preferably about 25 cm from the laryngoscope.

In one particular embodiment of the method of this invention, selected lesions of the epiglottis that invade the pre-epiglottic space can be diagnosed and can be treated by en bloc $CO_2$ laser excisional biopsy. Advantages of en bloc endoscopic excisional biopsy include: 1. short operating time (approximately 30 minutes); 2. avoidance of tracheotomy and neck incision; 3. overnight hospitalization and regular diet the day after surgery; 4. preservation of radiation for more advanced lesions. Previously, these lesions had to be managed with laryngectomy, pharyngotomy and excision, or full course radiation therapy. Endoscopic excisional biopsy is therefore a treatment option for selected early carcinomas of the supraglottic larynx and lower pharynx. Moreover, these lesions may have been overtreated in the past because of their endoscopic inaccessibility.

Before any excision is begun, each pharyngoepiglottic fold is grasped with a cup or an alligator forceps and a coagulating current is applied. This controls the major arterial supply to the operative site. The $CO_2$ laser is used to "cut" through each fold at the lateral edges of the epiglottis. With the tissue on maximum traction, these cuts are connected across the vallecular surface of the epiglottis. By continuing to follow the limits of the epiglottis, an en bloc excision may be accomplished. Careful dissection along the anterior surface of the epiglottis can facilitate biopsies of the pre-epiglottic space and can avoid significant bleeding. If necessary, the petiole of the epiglottis can also be excised. The tissue heals by secondary re epithelialization, without primary closure.

After epiglottectomy, the airway is always more open than the preoperative airway. A single bolus of dexamethasone sodium phosphate (1.0 mg/7.5 kg:10 mg in the adult) prior to induction of anesthesia can inhibit traumatic edema of the vocal cords. Tracheotomy is not needed. Another embodiment of the method is useful for rapid laser tumor debulking, an effective emergency treatment option for airway restoration in patients with obstructing laryngeal tumors such as untreated squamous carcinoma or in patients with post-radiation supraglottic edema. In patients with radiation-induced edema, the supraglottiscope is inserted and the superior blade placed in the vallecula. The upper body can be suspended as described previously. Awake, oral intubation can be performed and the edema is vaporized using a $CO_2$ laser. The laser is used to debulk enough of the edematous tissue mass to provide a safe, tubeless airway. Carbon dioxide laser laryngeal airway restoration avoids artificial airways, emergency laryngectomy, and complications from these procedures. It provides for, but does not interfere with, prompt, elective definitive surgery, irradiation, or chemotherapy.

The method of this invention will now be more fully described in the following examples.

EXAMPLE 1

Endoscopic Management of Early Supraglottic Cancer

This example illustrates use of the supraglottiscope in the staging and treatment of supraglottic cancer.

A. Surgical Technique

A foil wrapped Rusch endotracheal tube is used and is covered with a wet cottonoid. The supraglottiscope can be placed in the vallecula or under the epiglottis, depending upon which region of the supraglottis needs to be exposed. If a lesion on the epiglottis or on the aryepiglottic fold is to be removed, it is preferable for the superior blade to be in the vallecula. The supraglottiscope is inserted with the blades closed. After positioning the scope, the blades are fully separated and the inferior blade is additionally distended. This retracts the endotracheal tube into the interarytenoid space and out of the operative field. The patient is then placed into suspension.

To perform an epiglottec the vallecular mucosa is incised, exposing the hyoepiglottic ligament which is seen as a glistening white structure. The hyoepiglottic ligament is then incised and the dissection continued along the anterior surface of the epiglottis in the pre-epiglottic space. Gross cancer can sometimes be visualized penetrating the epiglottic fenestrations into the pre-epiglottic space. Once cancer is documented in the pre epiglottic space, it is considered to be advanced disease. The endoscopic procedure is terminated and definitive open laryngectomy or radiation therapy is performed. The type of laryngectomy is individualized to the patient and the disease. If there is no indication of pre-epiglottic space invasion, the local excision continues. The epiglottis is grasped with an alligator forceps which provides changes in the operative site as well as retraction. The mucosal margins of the cancer and the borders of the epiglottis are easily visualized and palpated. Hemostasis is obtained with electrocautery or a defocused laser spot. If the epiglottic lesion extends to the mucosa of the false cord, it is wise to first outline the lateral margins of the excision by placing the superior blade under the epiglottis. Similarly, if the lesion is on the false vocal cord, it is preferable for the superior blade to be under the epiglottis.

EXAMPLE 2

En bloc transoral subtotal supraglottic laryngectomy

One patient had a large T3 (extensive pre-epiglottic space invasion) supraglottic cancer confined to the supraglottis. Despite vigorous encouragement, he refused any form of open surgery. We therefore performed what is, to our knowledge and belief, the first en bloc subtotal supraglottic laryngectomy with clear surgical margins. This operation included both false cords, the epiglottis, as well as most of the pre epiglottic space and upper paraglottic spaces. This was a large excisional biopsy and the patient subsequently received full course radiation therapy to both the primary site and neck. Since completing his radiation, the patient has had two direct endoscopies confirming no evidence of recurrence at the primary site.

Clear surgical margins were obtained without the necessity of frozen section control. The patient healed by secondary re-epithelialization and there have been no episodes of local infection or chondritis. The patient did develop temporary aspiration which lasted 5 weeks.

The operating microscope and the $CO_2$ laser, in conjunction with the supraglottiscope of this invention, provide the head and neck surgeons with the capability of definitively separating patients with superficial cancer confined to the supraglottis from those with deep invasion. Endoscopic exploration of early appearing supraglottic cancer provides for accurate staging without precluding immediate routine treatment options of open surgery and/or radiation therapy. Advantages of endoscopic excision of early supraglottic cancer include short operating time, and no voice change except improvement if a superficial exophytic lesion is removed. There is no aspiration when the superficial disease is removed, therefore the patients can go home the day after surgery and they can resume their normal lifestyle. Endoscopic resection of early supraglottic cancer should accompany routine surgical options (supraglottic laryngectomy, near total laryngectomy, total laryngectomy) and radiation therapy.

The improvements described herein provide the adjustable supraglottiscope with several significant advantages over laryngoscopes currently available. The modifications described herein contribute to wide exposure of the supraglottis which results in easier and shorter surgical procedures. Use of the supraglottiscope in conjunction with suspension methods gives a wide view of the supraglottic larynx and lower pharynx, including the false vocal cords, the epiglottis, the base of tongue, the posterior oropharyngeal wall, aryepliglottic folds, arytenoids, upper pyriform sinus, and the post-cricoid region.

The endotracheal tube is retracted by the inferior blade of the supraglottiscope, thus preventing it from being displaced into the operative field and inhibiting exposure. The lumen created by the distal and proximal ends is such that instrumentation can be brought in from the side between the blades so as not to obscure the surgeon's vision. The adjustability allows for precise placement in different sized patients.

The shorter and wider blade of the supraglottiscope enable surgical procedures not possible with the longer and thinner blades of conventional laryngoscopes. For example, laser surgery of the epiglottis is difficult with conventional laryngoscopes because the instrument was designed to function deeper in the throat. Therefore the critical working distance between the laryngoscope and the microscope is shortened precluding the use of some hand held instrumentation used in laser microsurgery. The supraglottiscope eliminates the need to redefine the working distance and/or eliminates the necessity for redesigning the instrumentation needed for microsurgery.

EQUIVALENTS

Those skilled in the art will know, or be able to ascertain using no more than routine experimentation, many equivalents to the specific embodiments of the invention described herein. These and all other equivalents are intended to be encompassed by the following claims.

I claim:

1. In a laryngoscope, having a handle integrally connected to a blade means, said blade means including a pair of opposed, substantially parallel blades, the blades comprising a superior blade for engagement with at least part of the tongue and an inferior blade for engagement with at least part of the mouth roof of a patient, each blade having a proximal end defined as the end of said blade intended to be positioned farthest from the supraglottic larynx and a distal end defined as the end intended to be positioned closest to the supraglottic larynx a length defined as the distance substantially between said proximal end and said distal end, a width at each of said proximal and distal ends, and a length to distal width ratio calculated as the ratio between said length and said width at said distal end, an elongated lumen defined through the blades for reception of instruments and a means for urging the blades apart, wherein the improvement comprises:

a modified superior blade wherein the superior blade is at least as wide as a normal, human epiglottis and wherein the superior and inferior blades each have a length to distal width ratio of from about 4 to about 4.7, sufficient to expose the supraglottic larynx when the blades are engaged and urged apart.

2. The laryngoscope of claim 1 wherein the superior blade is from about 22 to about 28 mm wide.

3. The laryngoscope of claim 2 wherein the superior blade is about 110 mm long and the inferior blade is about 95 mm long.

4. The laryngoscope of claim 1, wherein the improvement further comprises:

an elongated lumen defined through the superior and inferior blades having a cross-sectional area of at least 1,000 $mm^2$ when the blades are fully urged apart.

5. The laryngoscope of claim 4, wherein the width of the superior blade is from about 22 to about 28 mm.

6. A method for performing surgery on the supraglottic larynx of a patient, comprising the steps of:

inserting an endotracheal tube into the patient's throat;

inserting a largyngoscope having a superior an and inferior blade into the patient's mouth, each blade having a proximal end defined as the end of each of said blades intended to be positioned farthest from the supraglottic larynx of the patient, a distal end defined as the end of each of said blades intended to be positioned closest to the supraglottic larynx of the patient, a length defined as the distance substantially between said proximal end and said distal end, a width at each of said proximal and distal ends, and a length to distal width ratio calculated as the ratio between said length and said width at said distal end, said superior blade being at least as wide as a normal, human epiglottis and wherein the blades have a length to distal width ratio of from about 4 to about 4.7 sufficient to both expose the supraglottic larynx and keep the endotracheal tube out of the operative field when the blades are engaged and urged apart;

engaging the inferior blade with at least part of the patient's mouth roof and the superior blade with at least part of the patient'tongue;

urging the blades apart to expose the supraglottic larynx; and engaging the laryngoscope with a lifting means of a suspension system.

7. The method of claim 6, wherein the step of inserting the blades comprises inserting the superior blade proximal to the vallecula, to expose base of the tongue.

8. The method of claim 6 wherein the step of inserting the blades comprises inserting the superior blade anterior to the epiglottis, to expose the epi-glottis, aryepiglottic folds, and medial walls of the pyriform sinus.

9. The method of claim 6 wherein the step of inserting the blades comprises inserting the superior blade posterior to the larynx, to expose the posterior pharyngeal wall.

10. The method of claim 6, wherein the step of inserting the blades comprises inserting the superior blade posterior to the epiglottis, to expose the false vocal cords and the arytenoid cartilages.

11. The method of claim 6, wherein the step of inserting the blades comprises inserting the superior blade on at least one side of the pharyngoepiglottic fold

* * * * *